Figure 1:
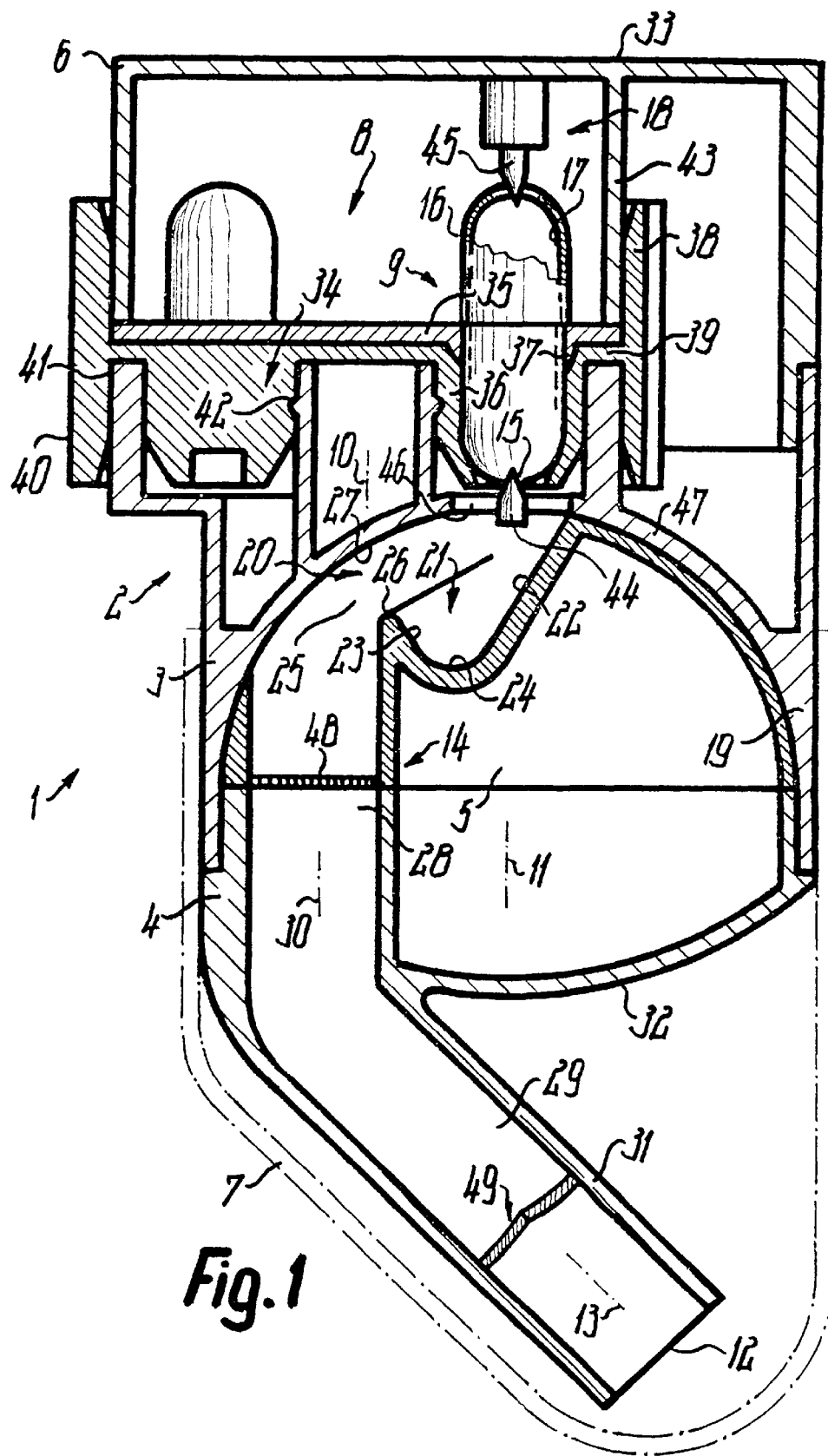

United States Patent [19]
Amann et al.

[11] Patent Number: 5,964,417
[45] Date of Patent: Oct. 12, 1999

[54] DISPENSER FOR DISCHARGING MEDIA

[75] Inventors: Esther Amann; Karl-Heinz Fuchs, both of Radolfzell, Germany

[73] Assignee: Ing. Erich Pfeiffer GmbH, Radolfzell, Germany

[21] Appl. No.: 08/966,377

[22] Filed: Nov. 7, 1997

[30] Foreign Application Priority Data

Nov. 20, 1996 [DE] Germany .............. 196 47 947

[51] Int. Cl.⁶ .................................. A61M 15/00
[52] U.S. Cl. .................... 239/338; 128/203.21
[58] Field of Search ............... 128/203.19, 203.21, 128/203.15, 203.28; 222/631, 344; 239/355, 357, 325, 337, 432, 399

[56] References Cited

U.S. PATENT DOCUMENTS

| | | | |
|---|---|---|---|
| 3,888,252 | 6/1975 | Side et al. | 128/203.21 |
| 4,778,054 | 10/1988 | Newell et al. | 128/203.12 |
| 5,113,855 | 5/1992 | Newhouse | 128/203.12 |
| 5,239,993 | 8/1993 | Evans | 128/203.15 |
| 5,320,714 | 6/1994 | Brendel | 128/203.15 |
| 5,366,122 | 11/1994 | Guentert et al. | 222/401 |
| 5,437,270 | 8/1995 | Braithwaite | 128/203.15 |
| 5,447,151 | 9/1995 | Bruna et al. | 128/203.19 |
| 5,503,144 | 4/1996 | Bacon | 128/205.19 |
| 5,522,383 | 6/1996 | Calvert et al. | 128/203.21 |

FOREIGN PATENT DOCUMENTS

| | | |
|---|---|---|
| 2 352 556 | 12/1977 | France . |
| 3811309 A1 | 10/1989 | Germany . |
| 4021263 A1 | 1/1992 | Germany . |
| 4133281 A1 | 4/1993 | Germany . |
| 4134665 A1 | 4/1993 | Germany . |
| 4208880 A1 | 9/1993 | Germany . |
| 4306458 A1 | 9/1994 | Germany . |
| 4415462 C1 | 8/1995 | Germany . |
| 1118341 | 7/1968 | United Kingdom . |
| 2300371 | 11/1996 | United Kingdom . |
| WO 95/03846 | 2/1995 | WIPO . |
| WO 95/24972 | 9/1995 | WIPO . |

OTHER PUBLICATIONS

German Search Report dated Sep. 10, 1997 in German Appl. No. 196 47 947.9.

*Primary Examiner*—Kevin Weldon
*Attorney, Agent, or Firm*—Quarles & Brady LLP

[57] ABSTRACT

A dispenser for discharging media has a duct (14) including a medium outlet (12), and a dosage carrier (34, 35) mounted on a base body (2) and including receptacles (36, 37) for receiving doses of the medium entirely enclosed in respective reservoir spaces (17), a medium holder (21) disposed beneath the reservoir spaces and adjacent the duct (14) for holding the medium when it is released from one of the reservoir spaces (17), and a device (44, 45) for opening one of the reservoir space (17) to allow the medium to be first deposited in the medium holder (21), and then picked up and conveyed out the medium outlet (12) by a transfer flow through the reservoir space (17).

27 Claims, 2 Drawing Sheets

DISPENSER FOR DISCHARGING MEDIA

TECHNICAL FIELD

The invention relates to a dispenser or discharge device for media which may be gaseous, liquid, pasty and/or powdery.

DESCRIPTION OF THE BACKGROUND ART

Such dispensers are simultaneously held and actuated or applied single-handedly. Substantially all parts, more particularly, housing parts can be made of a plastics material or injection molded so that their wall thickness is not more than 5 mm or 2 mm. The medium can be finely dispersed in a fluid flow, conveyed in a gas or air and discharged in individual quantities precisely dispensed and sufficiently swirled for this purpose within the dispenser by multiple deflection.

If the dispenser is intended to serve inhaling a pharmaceutical medium, the medium is expediently admixed in the conveying flow not before application, it previously being stored substantially more dense and compact.

OBJECTS OF THE INVENTION

An object of the invention is to provide a dispenser in which disadvantages of prior art embodiments are avoided. Another object is to ensure facilitated handling. Another object is to provide a most finely atomized discharge of medium. A further object is to precisely dose the amount of medium dispensed. Still another object is to permit administration of the medium deeply at the inner ends of the human respiratory ducts.

SUMMARY OF THE INVENTION

In the invention means are provided to very finely particulate the medium within the conveying paths of the dispenser, for example, by merely a single or multiple reciprocating motion of the medium so that already existing largish particles can be separated into smaller particles or droplets at at least two impact surface areas located opposite each other. In the case of a powder this may first gain access downwards into a dished impact or guiding surface area with or without an air flow, after which it is lifted by the air flow from this first surface area at high speed, swirled and catapulted against an opposite wall which results in any clumped powder particles being size-reduced. The proportion of respiratory particles, i.e. particles gaining access to the lungs of the patient is thus substantially enhanced as compared to such discharge devices which are merely intended for nasal application or for application of the medium in the region of the throat.

The cited first or any other surface area may be provided as a buffer storage or initial hold for at least part of the single-shot dose of the medium. During opening and, where necessary also thereafter, at least part of this dose of the flowable medium then falls on the troughed upwardly flared initial hold and it is not until the then occuring conveying flow that this medium is lifted swirled from the initial hold, after which it is immediately catapulted against the wall located thereabove before being redeflected in the falling direction from the reservoir to the outlet or mouthpiece.

Expediently by means of suitable sealing, the conveying flow flows through the reservoir space completely so that any remainders of the medium remaining therein are entrained up to the outlet. These remainders too, gain access from the reservoir with no contact directly to the initial hold which may feature inclined sliding surfaces so that the medium is able to gain access to the lowest point of the initial hold by its gravity effect even in the absence of a conveying flow.

Between the reservoir outlet and the initial hold a parting member may be provided for fanning out the medium flow, for example, a spike or a tip which also serves to open the reservoir and protrudes into the reservoir space or the medium contained therein.

The conveyance path between the reservoir and the outlet after which the medium emerges into the open in becoming totally detached from the discharge device, is configured to advantage as short as possible and as of the swirl zone as straight as possible or angled or curved at an obtuse angle once only to minimize flow losses. The path between the reservoir outlet and the swirl zone is shorter than the flow path between the middle of this swirl zone and the outlet, but maximally three-times as large. The middle of the swirl zone may coincide with the middle of the opposite impact surface area. The minimum passage cross-section of the conveyance paths which is to advantage smaller than the full-length constant passage cross-section of the reservoir space is located preferably at the transition point which is defined as the most constricted point of the two surface areas located opposite each other, it guiding the medium from the initial hold into the end passage leading to the outlet. This end passage may have a constant passage cross-section throughout.

The outlet as well as the straight end passage forming this outlet by one end are located at an angle to the reservoir or main axis of the device so that the latter can be held more or less vertically in an oral application with the head slightly tilted backwards and the thumb of the person using the device is located between upper lip and mouthpiece or in contact with both.

In the conveyance paths upstream and/or downstream of the reservoir space a valve may be provided which opens as a function of pressure so that it is not until a predetermined vacuum pressure is attained downstream of the valve that the conveying flow is abruptly set in motion through the opening of the valve, resulting in very high flow rates. The valve may be a sleeve valve.

These and further features are evident from the description and the drawings, each of the individual features being achieved by themselves or severally in the form of subcombinations in one embodiment of the invention and in other fields.

BRIEF DESCRIPTION OF THE DRAWINGS

Example embodiments of the invention are explained in more detail in the following and illustrated in the drawings in which:

FIG. 1 is an axial section through the discharge device in accordance with the invention, FIG. 2 is a partly sectioned view of the discharge device as shown in FIG. 1 as viewed from underneath and FIG. 3 is a scrap view of a further embodiment including a conveying flow pressurizer.

DETAILED DESCRIPTION OF PREFERRED EMBODIMENTS

The device 1 comprises a base body 2 of but five housing parts 3 to 7 of which in the readiness or operative condition merely three parts 3, 4, 6 firmly connected in common with a crib unit 8 form the completely outer surface area of the device 1. The part 5 is arranged totally countersunk firmly seated in the part 3 and directly located axially by the part 4. The unit 8 comprises at least four and not more than eight reservoir locations 9 for the medium arranged evenly distributed and directly juxtaposed in a circle about an axis 10. The axis 10 is located parallel to the main axis 11 in which the location 9 operative in each case is located to be discharged directly from this position for discharge through an outlet 12. The axis 13 of the latter is oriented at an obtuse angle of minimally 110° and maximally 160°, more particularly 135°, to the axis 10 or 11. As viewed parallel to the axis 10, 11 the outlet 12 is located totally within the outer circumference of the base body 2.

Provided totally within the base body 2 is a fluid guide 14 or passageway connecting the latter at both ends, between which a reservoir outlet 15 is located for discharging the medium. The outlet 15 has a substantially smaller spacing away from the upstream end of the guide 14 than from its outlet end 12. The outlet 15 is formed by one end of an elongated, separate reservoir body 16 having an elongated reservoir space 17 which in the emptying position is coaxial to the axis 11. The dimensionally rigid body 16 is formed by a two-part capsule of rigid gelatine or the like, the two shell-shaped parts of which are axially combined in a tight fit and the ends of which face away from each other are hemispherical so that the medium contained in the space 17 is sealingly packaged prior to opening of the device 18, filling the space 17 totally or merely partly as a single-shot dose. The body 16 or the space 17 which permits opening only by destruction forms in operation a section of the guide 14 extending over its full length, the openings of which located at the two ends are substantially more constricted in a throttle like action than the full-length constant passage cross-section of the portion of the space 17 located between the ends.

The exposed outer shell 19 formed merely by the parts 3, 4, 6, 8 of the device 1 can be clasped almost completely by a single hand. Within this shell 19 the guide 14 forms a zone 20 for swirling, size-reduction and atomized dispersion of the medium already entrained upstream by the air flow. In the middle between the ends of the guide 14 or device 1, in the operative position below the outlet 15 a dished or troughed initial hold 21 open only to the top is provided, the bottom 24 of which is spaced away from the outlet 15 by a spacing which is smaller than the length of the space 17. The concave curved bottom 24 adjoins a longer flank 22 and a shorter flank 23 which diverse upwards at an acute angle. The common axial plane of the surface areas 22 to 24 or bowl 21 located between the axes 10, 11 but nearer to the axis 10 is offset to one side of the axis 11 of the outlet 15 so that the outlet 15 is located vertically above the middle of the bottom 24 when the device 1 is slightly tilted rearwards in the operative position, the axis 13 thus being less inclined than in the vertical orientation of the axes 10, 11. The flank 22 sealingly adjoins the outlet 15 and the flank 23 extends only to a constricted transition point 25 between the bowl 21 and the part of the guide 14 located downstream thereof. The flank 23 extends to a rounded, lengthwise lip 26 which is located opposite a concave surface area 27 above the latter, this surface area 27 like the bowl 21 being curved about an axis located transversely at right angles to the axes 10, 11, but which has a radius of curvature larger than that of the bottom 24 by at least four or five times. The surface area 27 extends in and opposite to the direction of flow beyond the transition point 25 defining the lip 26, namely up to the outlet 15 and as a circumferential definition up to a straight passage section 28 adjoining upstream the transition point 25 and the lip 26.

The end of the section 28 located downstream adjoins an end passage 29 in an obtuse angled curvature, the end of the end passage forming the outlet 12. The axis 30 of the section 28 is located parallel to the axis 10, 11 and on the side of the axis 10 facing away from the axis 11. The two passage sections 28, 29 are straight and have a constant flow cross-section throughout which is greater than that of the transition point 25. The section 29 is formed by a freely protruding, tubular port 31 of constant outer cross-sections which as the mouthpiece is to be introduced over the majority of its length into the mouth of the patient, whose lips sealing surround it. In this arrangement the section 29 may be slightly longer than the section 28 up to the lip 26. Bowl 21 and port 31 are located on the same side of the section 28.

The bowl 21 including the surface areas 22 to 24, 26 and a first longitudinal section of the passage part 28 is defined exclusively by part 5 which is inserted totally countersunk as far as it will go in part 3 opposite the direction of flow and is axially located by the part 4 likewise inserted in this direction. This part 4 forms a longitudinal section of the passage part 28 adjoining the part 3 therewithin as well as the section 29, the port 21 and the outlet 12. The part 4 does not protrude beyond the outer circumference of part 3, it sealing contacting the lower annular face surface area of the latter by a ring shoulder. The surface area 27 extending over an angle of an arc of less than 90° and more than 45° is formed only by the part 3 as well as being smoothly continued at both ends so that it forms an intermediate section of a semi-circular or hemi-spherical or U-shaped impact surface area of the part 3, the part 5 sealingly contacting the continuations of the latter adjoining the surface area 27 by convex surface areas and subsequently thereto the part 4 by its circumferential surface area.

The flank 22 extends up to these curved surface areas and the flank 27 is passed through in the region of the outlet 15 as well as subsequent to the flank 22 by a transition opening 46 for the medium and the air flow. The passage cross-section of this transition opening 46 located in the axis 11 corresponds to the largest passage cross-section of the space 17, but the clearance of the transition opening 46 is larger than the largest clearance of the space 17. The bowl 21 is located between the axes 11, 30 and the largest clearance of the bowl 21 level with edge 26 is larger than the associated depth of this bowl 21. The definitions of the passage sections 21, 25, 28 location parallel to the plane of the drawing may be more or less flat as well as parallel to each other so that as viewed axially the device is web-shaped in the associated region. Like the cited surface areas this region may be rotationally curved about the axis 11, however.

Spaced away above the arrangements 12, 29, 31 part 4 of the body 2 forms a barrel-shaped handle 32 which adjoins the rear end of the outer circumference of the mouthpiece 31 in an inwardly directed acute angle at right angles transverse to the axis 11 and ascends to the region remote therefrom up to the outer circumference of the shell 19. The other handle 33 is formed by the rear end of the body 2, namely the outer side of the face end wall of the part 6 so that the two handles form a grip 32, 33 in which the thumb rests on the handle 32 and further fingers of the same hand clasp the handle 33 facing away from the latter, whilst the mouthpiece 31 is introduced between the lips of the patient and the finger supported by the convex handle 32 may be in contact with the upper lip of the patient as well as by its side facing away therefrom with the outer circumference of the mouthpiece 31. Throughout the complete operation and discharge of the device the handles 32, 33 are located rigidly positioned to each other.

The unit 8 comprises a crib body 34 movable about the axis 10 which is defined axially between the parts 3, 6 and carries replacably on its side facing the part 6 a crib insert 35 having the cited number of reservoir bodies 16. The body 34 comprises for each location 9 a sleeve-shaped mount 36 freely protruding in the direction of flow, this mount surrounding the one lower end of the body 16 in a tight seal and forming by a constriction a stop for the lower curved end surface area of the body 16. A mount 37 correspondingly protruding only in the direction of flow, but substantially smaller also comprises the insert 35 for each location 9. The crib body 34 and crib insert 35 provide a dosage carrier, and the mounting structures 36, 37 provide receptacles for receiving doses of the medium encapsulated within reservoir spaces 17. The mount 37 which protrudes only beyond the lower face side of the otherwise circular or disk-shaped flat insert 35 engages by a conical outer circumference a conical inner surface area at the rear end of the mount 36 so that it adjoins the outer circumference of the narrower part of the body 16 in a radially constricted seal, whereby the flared cap part of the body may adjoin by its face surface area the upper face surface area of the insert disk 35. As a result of this, this rear end or the cap part protrudes opposite to the direction of flow non-contactingly into the internal space of the part 6 whilst the lower longitudinal section is located totally in the mounts 36, 37 and passes through the bodies 34, 35. The body 34 which like each of the parts 3 to 7, 35 is configured integrally comprises at its outermost circumference a shell 38 at the inner circumference of which spaced away between its ends a face end wall 39 adjoins, beyond the undersides of which the mounts 36 protrude and adjoin the insert 35 at their upper face surface area. The outer circumference of the shell 38 forms a handle 40 and is located in an angle of an arc of minimally 90° or 160° and maximally 220°, more particularly only 180° about the axis 10 freely accessible at the outer circumference of the bodies 3, 6 for actuation. In the operative position the constricted end of the mount 36 surrounding the outlet 15 is located directly adjacent the transition opening 46 in the surface area 27 or adjacent to the outer side of the curved wall 47 which forms the surface area 27.

The body 34 located totally at this outer side is rotatably mounted directly on part 3 by two concentric bearings and is axially fixed in position in the opposite direction. The bearing parts configured integrally with the part 3 are formed by two nested bearing bodies such as sleeves freely protruding contrary to the direction of flow which slide on the underside of the wall 39 by their end surface areas. The outer sleeve of the bearing 41 slides by its outer circumference on the inner circumference of the shell 38 and by its inner circumference on the outer circumferences of the mounts 36. The inner sleeve of the bearing 42 slides by its outer circumference likewise on the outer circumferences of the mounts 36 which for this purpose form in common an inner circumference. Located between the two sleeves is the transition opening adjoining the outlet 15, the two sleeves translating integrally into the curved wall of the surface area 27. Since the sleeve of the bearing 41 is provided eccentrically to the axis 11 of the housing parts 3, 4 of the body 2 adjoining underneath, the sleeve protrudes beyond the parts 3, 4 at the side face away from the handle 32. For axial location a snap-action connector may be provided on one of the sleeves, more particularly between the outer circumference of the inner sleeve and the body 34 so that following completely removal of the part 6 the insert 35 including the emptied body 16 can be pulled out contrary to the direction of flow without releasing the body 34 from the bearings 41, 42.

A further radial and axial bearing is provided on the upper side of the bodies 35, 39 for which the shell 43 of the part 6 slides on this side at the inner circumference of the shell 38 and on the upper face surface area of the body 35, as a result of which the body 36 is held in close contact with the upper side of the wall 39. The shell 43 also forms only over part of the circumference the outer shell of the part 6 since the shell is located eccentrically relatively to this outer shell. Outside of the bearing member 43 this outer shell engages the interior of the shell of part 3 firmly seated, the outer shell being locked in place by a springy snap-action connector preventing removal except when a suitably high removal force is applied for removal contrary to the direction of flow. After this removal the body 35 is located with the bodies 16 freely accessible for replacement.

The device 18 comprises two opposing opening members 44, 45 in the axis 11 which may be formed by metal tips and serve to break open the end walls of the capsule 16 in the switching movement of the unit 8, as a result of which the capsule 16 is captured by the members 44, 45 in the last phase of translation into the operative position and is thus ruptured at the ends so that the tips protrude into the space 17, each being surrounded by a jagged opening. The member 44 passes through the associated transition opening 46 of the curved wall 47 after which it can be locked in place by the arms of a star-shaped mount. The outer circumference of this tip 44 forms a gliding surface area by which the medium and the air flow are flared into an envelope flow. The rear tip 45 is secured to the inner side of the face end wall of the part 3 so that the tips 44, 45 are oriented coaxially relative to each other.

For making use of the device 1 the ring 38, which may be provided with a means for indicating its rotary position and which has spring action to lock into each opening position, is turned until the next capsule 16 is located in the axis 11 and is then opened at both ends. Due to this opening action part of the medium trickles via the tip 44 along the flank 22 or 23 onto the bottom 24 of the bowl 21, i.e. after having left the tip 44 via a free-fall distance. After this the patient sucks on the mouthpiece 31 so that air is drawn in from without through openings in the housing space accommodating the upper end of the capsule 16 and the tip 45, the air flowing through the upper opening of the capsule 16 into the space 17.

The air flows through the space 17 entraining the remainder of the medium still left in this space 17, flows through the outlet 15 around the tip 44 directly into the opening 46 and from here against the flank 22 located nearer to the outlet 12 so that this conveying flow is diverted along the flank 22 and the bottom 24 back upwards as well as being directed directly against the surface area 27 on leaving the edge 26, the conveying flow thereby entraining the medium present in the bowl 21. In the region of the bowl 21 a rolling flow may briefly materialize, however, the conveying flow gains access whilst being accelerated due to the suction effect through the transition point 25 into the passage 28, 29 where mollification of the flow takes place which continues up to the outlet 12. On impinging against the surface area 27, opposite which the flank 23 is located on a direction of the radius the larger particles of the medium are reduced in size by the force of impact. For the next application the unit 8 is turned further to a location 9. The unit 8 is rotatable in one direction only, due to a free-wheel lock.

Downstream of the outlet 15 or the transition point 25 a sieve 48 or a filter inserted e.g. between the parts 3, 4 is provided in the passage 28 so that any fragments of the fractured capsule 16 or excessively large medium particles cannot gain access to the throat of the patient. Furthermore, a valve 49 may be provided in the flow path, namely upstream or downstream of the space 17, this valve opening as a function of the pressure being lower downstream than upstream. The opening force of this valve may be constant or reducing, the more the opening is made, so that the valve abruptly opens fully following commencement of the opening movement to release the conveying flow pulsedly. The valve 49 returning to its closed position as a function of the pressure may be located near to the outlet 12 within the passage 29 so that the section of the guidance 14 located upstream is sealingly closed off to prevent the ingress of any contamination during the non-active periods. The part 7 is configured as a protective cap which is to be completely removed axially prior to use of the device and in its protective position sealingly accommodates the port 31 including the opening 12 as well as the complete part 4 and the lower section of the part 3.

Figure 3:
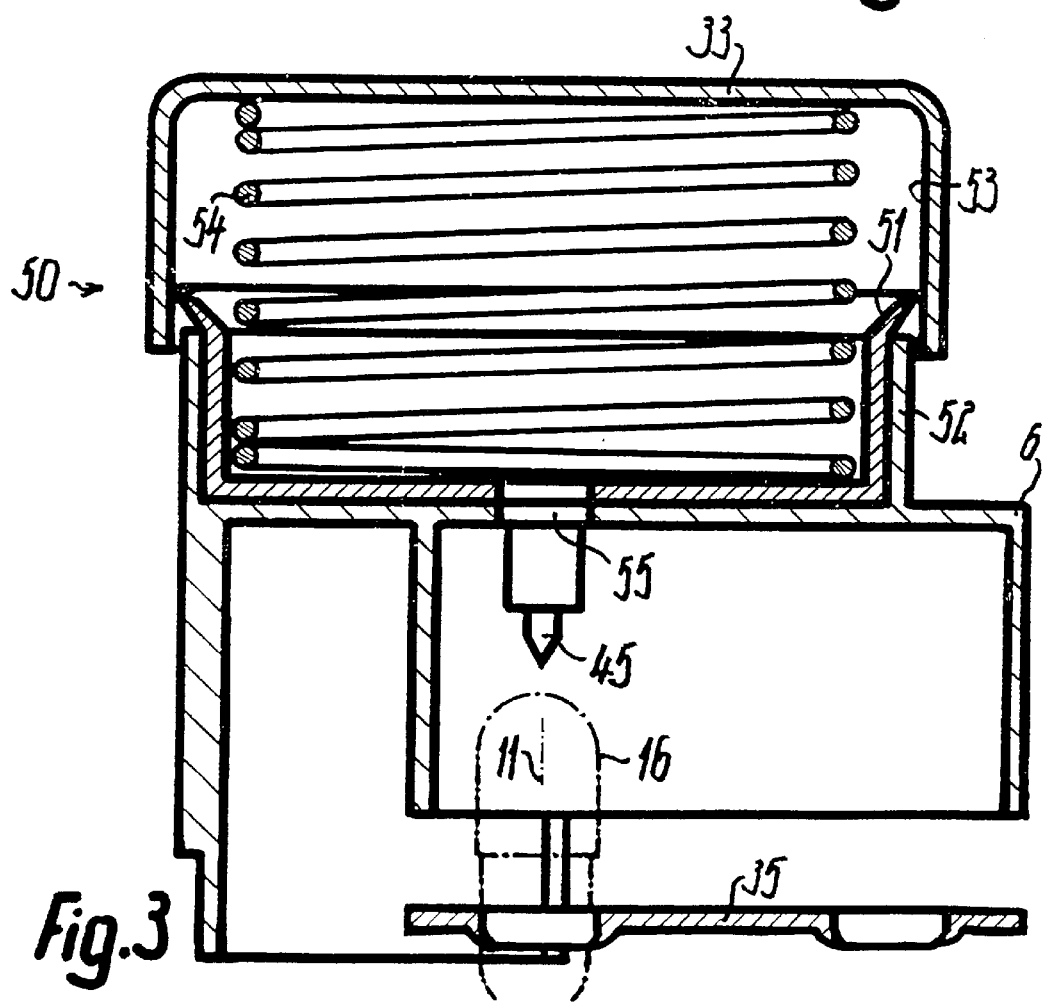

In FIG. 3 only the upper section of the device is shown as of part 6, on the underside of which an air pump 50 is arranged as a discharge actuator and pressure generator. Here, the upper face end wall of the part 6 does not form a handle, it instead comprising a shell 52 freely protruding upwards in which a dished piston 41 is inserted firmly in place by its shell as far as it will go against the face end wall of the part 6 so that its flared piston lip protrudes beyond the upper end of the shell 52. The piston lip slides on a cylinder 53 which closely surrounds the outer circumference of the shell 52 and which can be shifted downwards against the force of a spring 54 as far as it will go against the face end wall of the part 6 to supply air through an opening 55 in the crown of the piston as well as in the face end wall of the part 6 around the tip 45 of the capsule 16. The pump 50 is located in the axis 11 and the face end wall of the cylinder 53 forms the movable handle 33, on release of which the pump returns to its starting position in drawing in fresh air. Due to this action the path through the opening 55 may be closed off from suction by a valve, for example the valve 49. In this embodiment too, the air flow may be produced solely by suction action through the opening 12 and boosted at any time by actuating the pump 50. In FIG. 3 the insert 35 is shown in its change position by itself and without insert 34.

Figure 2:
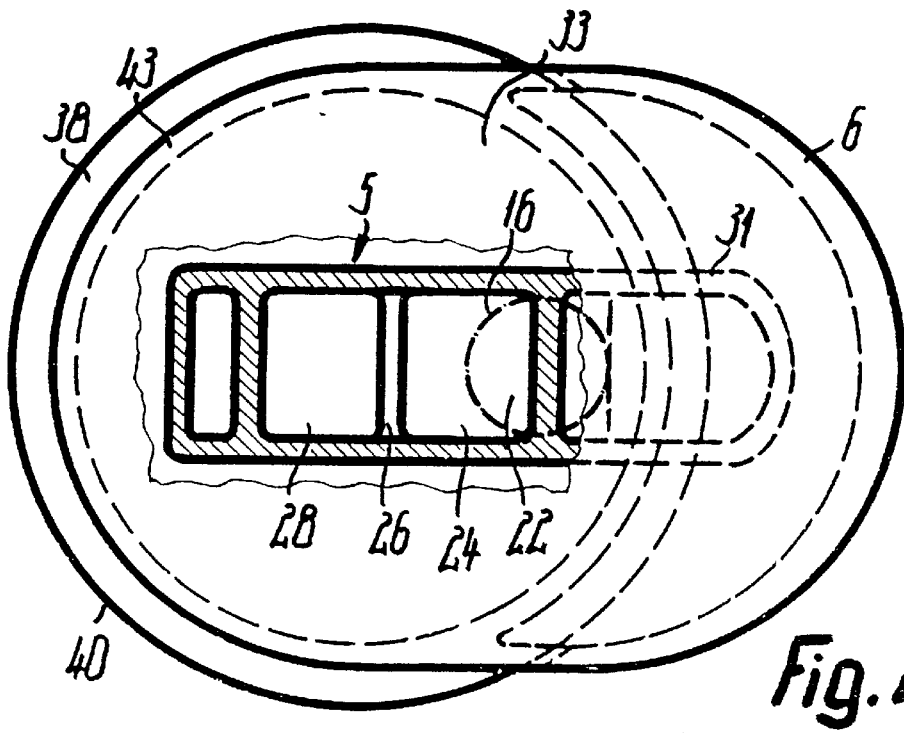

All cited effects and properties, such as positions, sizes and the like may be provided precisely as described, merely roughly so or substantially so and may also greatly vary therefrom, depending on the particular application. The device may be configured true to scale as depicted in FIGS. 1 to 3. The defining surface areas of the portions coming into contact with the medium, more particularly the portions 12, 14, 18, 20 to 29, 44 to 46, 48 and 49 may be provided with an anti-stick or anti-static coating of metal and/or a plastics material such as tetrafluoroethylene to prevent the medium tacking due to electrostatic charging. The coating is but a few mm thick and may be applied by spraying, bonding, pressurization or the like to the surface areas of the cited portions.

We claim:

1. A dispenser for discharging media comprising:

a base body (2) which can be manually oriented into a discharge position;

a dosage carrier (34, 35) including at least one receptacle (36, 37) for receiving a dose of the medium entirely enclosed in a reservoir space (17) while providing a predosed amount of the medium, said base body (2) supporting said receptacle (36, 37) when said dispenser (1) is in said discharge position, said reservoir space (17) having a top portion and having a bottom portion, which when opened, communicates with a reservoir outlet (15);

duct means (14) including an outlet duct (28, 29) and a medium outlet (12) at which the medium leaves said dispenser (1), said duct means (14) guiding the medium from said reservoir outlet (15) to said medium outlet (12);

a discharge actuator operable for generating a transfer flow for conveying said predosed amount through said duct means (14) and out of said medium outlet (12);

an upwardly opening medium holder (21) located below said reservoir outlet (15) when said dispenser (1) is in said discharge position, said medium holder (21) including a bottom depression (24), a first side surface (22) and a second side surface (23) opposing said first side surface (22), said first side surface (22) and said second side surface (23) extending upwardly from said bottom depression (24) when said dispenser (1) is in said discharge position, said outlet duct (28, 29) being disposed downstream from said medium holder (21) and said second side surface (23); and means for opening (44, 45) said reservoir space (17) to allow said predosed amount to flow through said reservoir outlet (15) and drop into said upwardly opening medium holder (21); and wherein upon opening of the reservoir space (17), the transfer flow flows through said reservoir space (17), through said reservoir outlet (15) and into said medium holder (21) to lift up the predosed amount from said bottom depression (24) in said medium holder (21) and over said second side surface (23), such that the predosed amount flows through the duct means and out of said medium outlet (12).

2. The dispenser according to claim 1, wherein upstream of said medium outlet (12) means are provided for disintegrating the medium into fine medium particles and for spacedly expanding the disintegrated medium particles, said disintegrating means (20) directly connecting to said second side surface (23) located downstream of said first side surface (22).

3. The dispenser according to claim 2, wherein said disintegrating means (20) include at least one of said duct means (14), an accelerator for accelerating the transfer flow, a swirl chamber for whirling the medium, an impact face (27) for rebounding the medium, and a sieve (48).

4. The dispenser according to claim 1, wherein a descent path is provided and directly connects said reservoir outlet (15) with said medium holder (21) for gravitationally descending and thereby transferring the medium from said reservoir outlet (15) into said medium holder (21), said descent path including a descent section for gravitationally dropping the medium into said medium holder (21) when said dispenser (1) is in said discharge position.

5. The dispenser according to claim 4, wherein said first side surface (22) and said second side surface (23) and said descent path includes a descent guide flowingly guiding and stationarily accumulating the medium in said bottom depression (24), said descent path extending continuously from said reservoir outlet (15) up to said bottom depression (24).

6. The dispenser according to claim 1, wherein said first side surface (22) and said second side surface (23) define a funnel open and actually widened toward said reservoir outlet (15) when said dispenser (1) is in said discharge position.

7. The dispenser according to claim 1, wherein said bottom depression (24) a concavely arcuated, said outlet duct including a first duct section (28) and a duct transition passage (25) directly interconnecting said medium holder (21) and said first duct section (28) located downstream of said bottom depression (24), said first duct section (28) defining a first passage cross-section and said transition passage (25) defining a transition cross-section smaller than said first passage cross-section.

8. The dispenser according to claim 1, wherein said first side surface (22) is closed up to said reservoir outlet (15), said second side surface (23) bounding a transfer aperture (25) connecting to said outlet duct (28, 29) upstream of said medium outlet (12), said outlet duct (28, 29) being bounded by a duct boundary, in axial cross-section through said outlet duct (28, 29) said second side surface (23) connecting to said duct boundary with a projecting transition lip (26).

9. The dispenser according to claim 8, wherein said medium holder (21) is a reception groove, said first side surface (22) being higher than said second side surface (23), downstream of said medium holder (21) said outlet duct (28, 29) being angular in said axial cross-section.

10. The dispenser according to claim 1, wherein said outlet duct (28, 29) continuously descends from said supply reception (21) up to said medium outlet (12) when said dispenser is in said discharge position.

11. The dispenser according to claim 1 and further defining a duct transition (25) between said second side surface (23) and said outlet duct (28, 29), wherein said duct transition (25) and said outlet duct (28) are bounded by a guide face (27) spacedly opposing said medium holder (21), when seen in axial cross-section through said outlet duct (28, 29) said guide face (27) being continuously concave from above said medium holder (21) up to downstream of said duct transition (25).

12. The dispenser according to claim 1, wherein in top plan view said outlet duct (28, 29) traverses said medium holder (21) when said dispenser (1) is in said discharge position, said medium holder (21) bounding a swirl chamber swirling the transfer flow while picking up the medium from the medium holder (21) and prior to entering said outlet duct (28, 29).

13. The dispenser according to claim 1, wherein said reservoir space (17) includes a reservoir inlet remote from said reservoir outlet (15) and traversed by the transfer flow, when said dispenser (1) is in said discharge position said reservoir inlet being located above said reservoir outlet (15).

14. The dispenser according to claim 13, wherein said reservoir space (17) is bounded by an entirely closed capsule (16) filled with said predosed amount, and wherein said manually actuable opening means (44, 45) is included for manually opening said reservoir space (17) at said reservoir outlet (15) and said reservoir inlet by rupturing said capsule (16).

15. The dispenser according to claim 14, wherein said opening means (44, 45) primarily open said reservoir outlet (15) upon a first opening motion defining a first opening direction and subsequently open said reservoir inlet upon a second opening motion oriented transverse to said first opening direction.

16. The dispenser according to claim 1, wherein said dosage carrier (34, 35) includes a plurality of individual receptacles (36, 37) separately receiving a plurality of the single discharge doses, said single discharge doses being consecutively transferable to be emptied into said medium holder (21), a magazine body (34) being provided and including said individual receptacles (36, 37), said magazine body (34) being displaceably mounted on said base body (2) for successively aligning each of said individual receptacles (36, 37) with said medium holder (21).

17. The dispenser according to claim 1, wherein said base body (2) includes an exterior casing assembled from a plurality of casing members (3 to 6) including a first casing member (3) and a second casing member (5) separate from said first casing member (3), in cross section through and along said duct means (14) said casing members (3 to 6) commonly and individually bounding said duct means (14), said medium holder (21) being entirely bounded by said second casing member (5), said first casing member (3) including a deflection face (27) spacedly opposing said bottom depression (24) and said first side surface (22) and said second side surface (23), said deflection face (27) being traversed by a supply opening (46) supplying both the medium and the transfer flow from said reservoir space (17) directly into said medium holder (21) and from said medium holder (21) directly into said outlet duct (28, 29).

18. The dispenser according to claim 1, wherein said base body (2) includes a casing member (5) including said medium holder (21) and made in one part, said casing member (5) defining a first member side including said medium holder (21), said casing member (5) defining a second member side remote from said first member side and bounding the medium holder (21), said base body (2) including an exterior base member (3), said casing member (5) being a component separate from said exterior base member (3) and entirely counter-sunk within said exterior base member (3), said exterior base member (3) defining an insertion side remote from said receptacle (36, 37), said casing member (5) being inserted into said exterior base member (3) from said insertion side.

19. The dispenser according to claim 1, wherein said base body (2) includes a subcasing (3, 5) assembled from first and second casing members (3, 5) and defining a first subside and a second subside remote from said first subside, said subcasing internally entirely enclosing said medium holder (15), at said first subside a first casing cover (6) being directly attached to said first and covering casing member (3) said receptacle (36, 37) at said second subside a second casing cover (4) being directly attached to said first casing member (3) and including said media outlet (12), said second casing cover (4) covering said second casing member (5) located within said first casing member (2) and including said medium holder (21).

20. (Amended) The dispenser according to claim 1, wherein said discharge actuator includes means for generating the transfer flow exclusively in response to human inhalation of air through said reservoir space (17) and said medium holder (21).

21. The dispenser according to claim 20, wherein said discharge actuator includes pump means (50) for positively generating the transfer flow through said medium space (17) in a selectable alternative operating mode, said reservoir outlet (15) directing the transfer flow directly into said medium holder (21).

22. The dispenser according to claim 1, wherein said duct means (14) are at least partly covered with a coating conducting the medium.

23. The dispenser according to claim 1, wherein in plan view said medium holder (21) and said outlet duct (28, 29) are commonly laterally bounded by opposite boundaries oriented transverse to said first side surface (22) and said second side surface (23), at least one of said opposite boundaries being substantially planar, said second side surface (23) including a lip (26) projecting from said second side surface for separating said medium holder (21) from said outlet duct (28, 29).

24. The dispenser according to claim 1, wherein said base body (2) includes a first end portion enveloping said receptacle (36, 37), said body base (2) including a second end portion enveloping said medium holder (21) and including said medium outlet (12), in a view against said medium outlet (12) said second end portion defining a web structure significantly less wide than said first end portion, said medium holder (21) being located within said web structure.

25. The dispenser according to claim 1, wherein said base body (2) includes a stud (31) freely projecting, longitudinally traversed by said outlet duct (28, 29) and including said medium outlet (12), a shield (32) circumferentially spaced from and opposing said stud (31) for operationally receiving a user's finger between said stud (31) and said shield (32).

26. The dispenser according to claim 25, wherein in planview said medium outlet (12) is located within said shield (32), said stud projecting at an angle from said shield (32).

27. The dispenser according to claim 1, wherein said reservoir space (17) has a vertical length and a horizontal width smaller than said vertical length when said dispenser (1) is in said discharge position.

* * * * *